(12) United States Patent
Anstett-Klein et al.

(10) Patent No.: US 8,703,192 B2
(45) Date of Patent: *Apr. 22, 2014

(54) DOSAGE FORM CONTAINING PANTOPRAZOLE AS ACTIVE INGREDIENT

(75) Inventors: Isabel Anstett-Klein, Leinfelden-Echterdingen (DE); Rango Dietrich, Constance (DE); Hartmut Ney, Constance (DE); Marc Schiller, Radolfzell (DE); Sabine Schaefer-Preuss, Singen (DE); Manfred Hartmann, Constance (DE)

(73) Assignee: Takeda GmbH, Constance (DE)

( * ) Notice: Subject to any disclaimer, the term of this patent is extended or adjusted under 35 U.S.C. 154(b) by 88 days.

This patent is subject to a terminal disclaimer.

(21) Appl. No.: 12/385,280

(22) Filed: Apr. 3, 2009

(65) Prior Publication Data

US 2009/0208571 A1 Aug. 20, 2009

Related U.S. Application Data

(63) Continuation of application No. 10/555,238, filed as application No. PCT/EP2004/050729 on May 7, 2004.

(30) Foreign Application Priority Data

May 8, 2003 (EP) ..................................... 03010328
Jan. 28, 2004 (EP) ..................................... 04001754

(51) Int. Cl.
  *A61K 9/22* (2006.01)
(52) U.S. Cl.
  USPC .......................................... 424/468; 424/471
(58) Field of Classification Search
  None
  See application file for complete search history.

(56) References Cited

U.S. PATENT DOCUMENTS

| | | | |
|---|---|---|---|
| 4,758,579 A | 7/1988 | Kohl et al. | |
| 4,786,505 A | 11/1988 | Lovgren et al. | |
| 5,183,662 A | 2/1993 | Morita et al. | |
| 5,997,603 A | 12/1999 | Noro et al. | |
| 5,997,903 A * | 12/1999 | Dietrich et al. ............... | 424/482 |
| 6,132,770 A | 10/2000 | Lundberg | |
| 6,248,363 B1 | 6/2001 | Patel et al. | |
| 6,346,269 B1 | 2/2002 | Hsiao et al. | |
| 6,346,569 B1 | 2/2002 | Irizato et al. | |
| 6,365,184 B1 | 4/2002 | Depui et al. | |
| 6,410,569 B1 | 6/2002 | Kohl | |
| 6,420,473 B1 * | 7/2002 | Chittamuru et al. .......... | 524/447 |
| 6,613,354 B2 * | 9/2003 | Depui et al. .................. | 424/458 |
| 6,677,362 B1 | 1/2004 | Ghebre-Sellassie et al. | |
| 2001/0008899 A1 * | 7/2001 | Gray .............................. | 514/338 |
| 2003/0003058 A1 * | 1/2003 | Linder et al. .................... | 424/46 |
| 2008/0305231 A1 | 12/2008 | Kojima et al. | |

FOREIGN PATENT DOCUMENTS

| | | |
|---|---|---|
| DE | 39 01 151 A1 | 7/1990 |
| EP | 0 005 129 B1 | 10/1979 |
| EP | 0 166 287 B1 | 1/1986 |
| EP | 0 174 726 A1 | 3/1986 |
| EP | 0 244 380 A1 | 11/1987 |
| EP | 0 268 956 A2 | 6/1988 |
| EP | 0 277 741 B1 | 8/1988 |
| EP | 0 282 131 B1 | 9/1988 |
| EP | 0 342 522 B1 | 11/1989 |
| EP | 0 474 098 A1 | 3/1992 |
| EP | 0 519 365 A1 | 12/1992 |
| EP | 0 960 620 A1 | 12/1999 |
| EP | 1 037 634 B1 | 9/2000 |
| EP | 1105105 | 6/2001 |
| EP | 1 187 601 B1 | 3/2002 |
| EP | 1 213 015 A1 | 6/2002 |
| EP | 1341528 | 9/2003 |
| JP | 11-343231 | 12/1999 |
| WO | WO 96/01623 A1 | 1/1996 |
| WO | WO 97/02020 A1 | 1/1997 |
| WO | WO 97/41114 A1 | 11/1997 |
| WO | WO 99/27917 A1 | 6/1999 |
| WO | WO 99/32091 A1 | 7/1999 |
| WO | 00/09092 | 2/2000 |
| WO | WO 00/09092 A1 | 2/2000 |
| WO | WO 00/10995 A1 | 3/2000 |
| WO | WO 0010995 A1 * | 3/2000 |
| WO | WO 02/39980 A2 | 5/2002 |
| WO | 02/045694 | 6/2002 |
| WO | WO 02/45692 A1 | 6/2002 |
| WO | WO 02/45694 A1 | 6/2002 |
| WO | WO 2004/098577 A2 | 11/2004 |
| WO | WO 2005/032513 A2 | 4/2005 |
| WO | WO 2005/107721 A2 | 11/2005 |
| WO | 2005/115161 A1 | 12/2005 |

OTHER PUBLICATIONS

Pohle and Domschke, Langenbeck's Arch Surg 385: p. 317-323, 2000.*
Bühler, V., "Polyvinylpyrrolidone for the Pharmaceutical Industry," *Kollidon-BASF*, 2nd edition, 1995, pp. 1-287.
Yoshida Hiromitsu, et al., Method to Increase Solubility, 1995, pp. 74-80.
Product Monograph for Tecta, Dec. 1, 2008.

* cited by examiner

*Primary Examiner* — Nissa Westerberg
(74) *Attorney, Agent, or Firm* — Nath, Goldberg & Meyer; Sheldon M. McGee (57) ABSTRACT

Dosage forms for the oral administration of the magnesium salt of pantoprazole are described.

9 Claims, 2 Drawing Sheets

DOSAGE FORM CONTAINING PANTOPRAZOLE AS ACTIVE INGREDIENT

This application is a continuation application of U.S. Ser. No. 10/555,238, now abandoned, which was filed Nov. 1, 2005 under 35 U.S.C. 371 as a national stage of PCT/EP2004/050729, filed May 7, 2004.

TECHNICAL FIELD

The present invention relates to the field of pharmaceutical technology and describes a dosage form for oral administration of the magnesium salt of pantoprazole. The invention additionally relates to processes for producing the dosage form.

PRIOR ART

It is generally known to coat peroral administration forms, e.g. tablets or pellets which contain an acid-labile active compound, with an enteric coating which, after passage through the stomach, rapidly dissolves in the alkaline medium of the intestine. Examples of such acid-labile active compounds are acid-labile proton pump inhibitors ($H^+/K^+$ ATPase inhibitors), in particular pyridin-2-ylmethylsulfinyl-1H-benzimidazoles, such as are disclosed, for example, in EP-A-0 005 129, EP-A-0 166 287, EP-A-0 174 726 and EP-A-0 268 956. On account of their $H^+/K^+$ ATPase inhibiting action, these are of importance in the therapy of diseases, which are due to increased gastric acid secretion. Examples of active compounds from this group which are commercially available are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoro-ethoxy)-2-pyridinyl)methylsulfinyl]-1H-benzimidazole (INN: lansoprazole) and 2-{[4-(3-methoxypropoxy)-3-methylpyridin-2-yl]-methylsulfinyl}-1H-benzimidazole (INN: rabeprazole).

Because of their strong tendency to decompose in a neutral and, in particular, in an acidic environment, where strongly colored decomposition products are also formed, for oral preparations it is also necessary in this case to protect the active compounds from the action of acids. In the case of the strongly acid-labile pyridin-2-ylmethylsulfinyl-1H-benzimidazoles, it is moreover necessary to process these in the tablet core or in pellets in the form of their alkaline salts, for example as sodium salts, or together with alkaline substances. Since the substances suitable for enteric coatings are those having free carboxyl groups, the problem results that the enteric coating is partly dissolved or even dissolved from inside because of the alkaline medium in the interior and the free carboxyl groups promote the decomposition of the active compounds. It may therefore be necessary to provide an isolating intermediate layer (subcoating) between the enteric coating and the alkaline tablet core or pellet. It is proposed in EP-A-0 244 380 to coat cores which contain the active compound together with alkaline compounds or as an alkaline salt with at least one layer of nonacidic, inert pharmaceutically acceptable substances, which are soluble in water or rapidly decompose in water, before the enteric layer is applied. The intermediate layer or intermediate layers act as pH-buffering zones in which the hydrogen ions diffusing in from outside can react with the hydroxyl ions diffusing from the alkaline core. In order to increase the buffer capacity of the intermediate layer, it is proposed to incorporate buffer substances into the intermediate layer(s). In practice, it is possible by this process to obtain somewhat stable preparations. However, relatively thick intermediate layers are needed in order to avoid the unsightly discolorations occurring even in the case of only slight decomposition. Moreover, a considerable effort is to be made in the preparation to avoid traces of moisture.

In EP-A-0 519 365, a formulation on the principle of the alkaline core coated with a water-soluble intermediate layer and an enteric coating is proposed for the active compound pantoprazole, in which improved stability is achieved by use of polyvinylpyrrolidone and/or hydroxypropylmethylcellulose as binders for the alkaline core. It is disclosed that as binder a polyvinylpyrrolidone of higher molecular weight is used.

EP-A-0 342 522 discloses a formulation for acid-sensitive benzimidazoles in which, between the alkaline core and the enteric coating, an intermediate layer is located which is composed of only slightly water-soluble film-forming material, such as ethylcellulose and polyvinyl acetate, and a slightly water-soluble finely granular inorganic or organic material suspended therein, such as, for example, magnesium oxide, silicon oxide or sucrose fatty acid esters.

EP-A-0 277 741 describes spherical granules having a core which is coated with spray powder, which contains low-substituted hydroxypropylcellulose and a benzimidazole compound having anti-ulcer activity. These granules can be coated with an enteric coating agent.

EP-A-1 213 015 discloses an oral pharmaceutical composition with delayed release of proton pump inhibitors.

As the abovementioned prior art shows, the production of peroral administration forms for acid-labile active compounds requires technically complicated processes.

The International Patent Application WO97/41114 describes a specific process for the preparation of magnesium salts of pyridin-2-ylmethylsulfinyl-1H-benzimidazoles. Inter alia, the preparation of the magnesium salt of pantoprazole is also described by way of example. According to the analysis data indicated, the salt prepared is pantoprazole magnesium in anhydrous form.

International Patent Application WO00/10995 describes the dihydrate of the magnesium salt of pantoprazole. It is disclosed that the dihydrate of the magnesium salt of pantoprazole has inter alia improved stability properties as in comparison to pantoprazole itself or to pantoprazole sodium sesquihydrate.

DESCRIPTION OF THE INVENTION

It is an object of the present invention to provide a dosage form for oral administration of pantoprazole magnesium salt, which dosage form can be produced without great technical complexity, which takes account of the acid lability of pantoprazole and which makes available the pantoprazole magnesium salt effectively for the body in such a way that an optimal active ingredient profile and thus action profile is achieved.

Pantoprazole magnesium oral pharmaceutical dosage forms, available as delayed release forms are found in-vitro to have prolonged dissolution times as compared to corresponding dosage forms containing pantoprazole sodium. From a pharmacokinetic point of view it may thus be expected that pantoprazole magnesium oral dosage forms may have clinical disadvantages, e.g. delayed onset of action as compared to pantoprazole sodium oral dosage forms. Surprisingly, it has been found now that pantoprazole magnesium oral dosage forms have unexpected release profiles of active ingredient and clinical advantages.

In one aspect the invention therefore relates to an oral pharmaceutical dosage form comprising pantoprazole magnesium together with pharmaceutically acceptable excipients.

Surprisingly it has also been found now that oral dosage forms for pantoprazole magnesium salt comprising low molecular weight polyvinylpyrrolidone as excipient show stability and a distinctly improved release profile for the active ingredient as compared to oral dosage forms for pantoprazole magnesium salt known from the art.

The invention therefore also relates to a dosage form for oral administration of pantoprazole magnesium salt comprising a therapeutically effective amount of the pantoprazole magnesium salt together with low molecular weight polyvinylpyrrolidone and one or more other suitable pharmaceutical excipients.

A dosage form means, in particular, a medicinal dosage form such as a tablet, a coated tablet, a multi-particulate form such as pellets or pellets and microtablets in a capsule or a multiple unit tableted dosage form (such as disclosed in WO 96/01623), with the dosage form advantageously being designed so that the pantoprazole magnesium salt is released, or made available effectively for the body, in such a way that an optimal active ingredient profile, and thus action profile, is achieved. Unit in connection with the multiple unit tableted dosage form refers to an individual unit containing the pantoprazole magnesium salt, which individual unit can be a small bead, particle, granule or pellet, in connection with the invention also referred to as pellet. Suitable dosage forms are for example disclosed in EP-A-0 519 365, EP-A-0 244 380, EP-A-1 213 015, EP-A-1 105 105, EP-A-1 037 634, EP-A-1 187 601 and EP-A-1 341 528.

The oral dosage form of the invention is preferably a dosage form with modified release of the active ingredient, in particular with delayed release of active ingredient. Particularly preferred is an enteric coated dosage form, comprising at least one enteric coating layer which is stable and does not release the active ingredient under acidic conditions but rapidly dissolves in neutral conditions and in particular in the alkaline medium of the intestine. In a further preferred embodiment the dosage form according to the invention in addition to the enteric coating layer contains one or more intermediate layers (subcoating layers). In another embodiment the dosage form according to the invention comprises at least one enteric coating layer but does not contain an intermediate layer.

Pantoprazole is the INN (International Nonproprietary Name) for the compound 5-difluoromethoxy-2-[(3,4-dimethoxy-2-pyridinyl)methylsulfinyl]-1H-benzimidazole. The magnesium salt of pantoprazole is the chemical compound magnesium bis[5-[difluoromethoxy]-2-[[3,4-dimethoxy-2-pyridinyl]methyl]sulfinyl]-1H-benzimidazolide]. In connection with the invention the pantoprazole magnesium salt can also be present in hydrate form (e.g. monohydrate, sesquihadrate or dihydrate). A particular preferred hydrate in connection with the invention is the dihydrate of the magnesium salt of pantoprazole with the chemical name magnesium bis[5-[difluoromethoxy]-2-[[3,4-dimethoxy-2-pyridinyl]methyl]sulfinyl]-1 Hbenzimidazolide]dihydrate. The synthesis of the magnesium salt of pantoprazole is described for example in International Patent Application WO97/41114 and the synthesis of the dihydrate of the magnesium salt of pantoprazole is disclosed in International Patent Application WO00/10995.

Because of a great tendency to decompose in a neutral and, in particular, acidic environment, which also results in highly colored decomposition products, for oral compositions, it is preferred on the one hand to keep the magnesium salt of pantoprazole in an alkaline environment and, on the other hand, to protect it from exposure to acids. It is generally known to coat tablets or pellets, which contain an acid-labile active ingredient with an enteric coating which, after passage through the stomach, rapidly dissolves in the alkaline medium in the intestine. In the case of pantoprazole, which is very acid-labile, it is preferred to process it in the tablet core or in pellets in the form of its alkaline salts, and preferably together with alkaline substances. Since the substances suitable for enteric coatings contain free carboxyl groups, a problem arises when the enteric coating is partly or even completely dissolved from the inside because of the alkaline medium in the interior, and the free carboxyl groups promote decomposition of the active ingredients. It is therefore preferred to provide a sealing intermediate layer (subcoating) between the enteric coating and an alkaline tablet or pellet core. EP-A 0244380 proposes to coat cores, which contain the active ingredient together with alkaline compounds or as alkaline salt with at least one layer, which is soluble in water or rapidly disintegrates in water, of nonacidic, inert pharmaceutically-acceptable substance before the enteric layer is applied.

The intermediate layer or intermediate layers act as pH-buffering zones in which hydrogen ions, which diffuse in from the outside, are able to react with the hydroxyl ions which diffuse out of the alkaline core. In order to increase the buffer capacity of the intermediate layer, it is proposed to incorporate buffer substance into the intermediate layer(s). It is possible in practice by this method to obtain rather stable compositions.

The invention therefore also relates to an oral dosage form in pellet or tablet form for magnesium salt of pantoprazole comprising a therapeutically effective amount of the magnesium salt of pantoprazole together with one or more other pharmaceutical excipients in a pellet or tablet core, at least one subcoating (intermediate layer) and an outer enteric layer which is soluble in the small intestine.

The invention further relates to an oral dosage form in pellet or tablet form for magnesium salt of pantoprazole comprising a therapeutically effective amount of the magnesium salt of pantoprazole together with one or more other pharmaceutical excipients in an alkaline pellet or tablet core, at least one subcoating (intermediate layer) and an outer enteric layer which is soluble in the small intestine.

In another embodiment the invention also relates to an oral dosage form in pellet or tablet form for magnesium salt of pantoprazole comprising a therapeutically effective amount of the magnesium salt of pantoprazole together with polyvinypyrrolidon and optionally one or more other pharmaceutical excipients in an alkaline pellet or tablet core, at least one subcoating (intermediate layer) and an outer enteric layer which is soluble in the small intestine.

In another embodiment the invention also relates to an oral dosage form in pellet or tablet form for magnesium salt of pantoprazole comprising a therapeutically effective amount of the magnesium salt of pantoprazole together with PVP90 and optionally one or more other pharmaceutical excipients in an alkaline pellet or tablet core, at least one subcoating (intermediate layer) and an outer enteric layer which is soluble in the small intestine.

In another embodiment the invention also relates to an oral dosage form in pellet or tablet form for magnesium salt of pantoprazole comprising a therapeutically effective amount of the magnesium salt of pantoprazole together with low molecular weight polyvinypyrrolidon and optionally one or more other pharmaceutical excipients in an alkaline pellet or tablet core, at least one subcoating (intermediate layer) and an outer enteric layer which is soluble in the small intestine.

In one embodiment of the invention the oral dosage form is a multiple unit tableted dosage form, with individual enteric coating layered units containing pantoprazole magnesium salt and optionally other excipients.

Further suitable pharmaceutical excipients, which may be used in the dosage form according to the invention are pharmaceutical excipients such as fillers, (additional) binders, disintegrants or else lubricants and release agents. Other suitable excipients, which may be present in the dosage form of the invention are, for example, flavoring substances (such as flavors and sweeteners), buffer substances, preservatives, coloring substances (such as iron oxide yellow or red), wetting agents, surfactants (such as sodium laurylsulfate) or else emulsifiers. Flavors are usually added in a proportion of from 0.05 to 1% by weight. Other flavoring substances by way of example are acids such as citric acid, sweeteners such as saccharin, aspartame, cyclamate sodium or maltol, which are added according to the desired result.

Suitable binders which can be used for preparing the tablet or pellet core are polyvinylpyrrolidone (PVP), hydroxypropylmethylcellulose, hydroxypropylcellulose, sodium carboxymethylcellulose, gelatine, whereby PVP is preferred.

In a preferred embodiment the invention also relates to a dosage form for oral administration of pantoprazole magnesium salt comprising a therapeutically effective amount of the pantoprazole magnesium salt together with polyvinylpyrrolidone (PVP) as a binder and one or more other suitable pharmaceutical excipients.

The polyvinylpyrrolidone (PVP) employed as binder according to the invention can be of molecular weight in the range of 2,000-1,500,000. In one embodiment according to the invention PVP 90 (average molecular weight about 1,000,000-1,500,000) or PVP in the range of from 600,000 to 700,000 can be mentioned as preferred. In another embodiment of the invention the PVP is a water-soluble PVP with a low average molecular weight and is preferably used as binder in the dosage form. Low average molecular weight in connection with the invention refers to PVP with an average molecular weight below 300,000, preferably below 100,000, particularly preferably below 70,000, more particularly preferably below 60,000, most particularly preferred below 40,000. Examples, which may be mentioned, are Kollidon 12 PF (molecular weight 2,000-3,000), Kollidon 17 PF (molecular weight 7,000-11,000), Kollidon 25 (molecular weight 28,000-34,000) and Kollidon 30 (molecular weight 44,000-54,000), whereby Kollidon 25 is preferred.

The proportion (in percent by weight based on the finished dosage form) of PVP as a binder (and, where appropriate, additional other binders) may preferably be according to the invention from 0.5 to 15% by weight. The proportion of PVP is preferably from 1 to 5% by weight, particularly preferably from 1.5 to 3.5% by weight.

Suitable fillers in connection with the invention are mannitol, lactose, starch, cellulose and calcium phosphate, whereby mannitol is preferred. In one embodiment of the invention mannitol is the sole filler used for the oral dosage forms according to the invention.

For a basic reaction of the pellet or tablet core (=alkaline tablet or pellet core) it is mixed (where required increase in pH is not achieved simply by using an active-ingredient salt) with an inorganic base. Mention may be made in this connection of, for example, the pharmacologically-suitable (tolerable) alkali-metal, alkaline-earth-metal or earth-metal salts of weak acids and the pharmacologically-suitable hydroxides and oxides of alkaline-earth and earth metals. Sodium carbonate may be mentioned as a base to be emphasized by way of example.

Besides filler and binder, other ancillary substances, in particular lubricants and nonstick agents, and tablet disintegrants, are used in the manufacture of tablet cores. Examples of lubricants and nonstick agents, which may be mentioned, are higher fatty acids and their alkali-metal and alkaline-earth-metal salts, such as calcium stearate. Suitable disintegrants are, in particular, chemically inert agents. Tablet disintegrants, which may be mentioned as preferred, are crosslinked polyvinylpyrrolidone, crosslinked sodium carboxymethylcelluloses, sodium starch glycolate and pregelatinized starch.

In one embodiment of the invention the oral dosage form according to the invention is a tablet and comprises as excipients for the tablet core sodium carbonate, mannitol, crospovidone, polyvinylpyrrolidone and calcium stearate.

In another embodiment of the invention the oral dosage form according to the invention is in pellet form on the basis of nonpareilles/seeds and the pellet core comprises starch as excipient. It has been found surprisingly that by using starch as excipient in the pellet core (based on nonpareilles/seeds) the release of the pantoprazole magnesium from the pellet core is faster and increased as compared to pellets without starch in the pellet core. Suitable types of starch, which can be used in this connection are different types of starch such as corn starch, potato starch, rice starch, wheat starch, preferably pregelatinized starch and in particular pregelatinized corn starch (Starch 1500). In a preferred embodiment according to the invention the amount of pregelatinized starch present in the pellet core is in the range of 0.5-4% per weight (based on the total weight of the pellet core), particularly preferably in the range of 1-3% per weight.

The pellet core may contain additional excipients such as those mentioned above and those mentioned in connection with tablet cores (e.g. binders, stabilizers, disintegrants, surfactants and wetting agents). Wetting agents in this connection preferably refers to synthetic tensides (such as polysorbate, spans, brij), sulfate- and sulfonate salts of fatty acids (such as sodium dodecylsulfate), non-ionic tensides (such as poloxamer) and glycerol esters of fatty acids. In a preferred embodiment SDS (sodium dodecylsulfate) is present. Binders, which may be present are for example PVP, HPMC, hydroxypropylcellulose (HPC) and gelatine. Disintegrants, which may be present are crosslinked polyvinylpyrrolidone, crosslinked sodium carboxymethylcelluloses and sodium starch glycolate.

In another embodiment of the invention the oral dosage form according to the invention comprises as excipients sodium carbonate, sodium laurylsulfate, pregelatinized starch, polyvinylpyrrolidone and sucrose [Pellets]. The oral dosage form is preferably a pellet on the basis of nonpareilles.

In respect of the intermediate layer(s) to be applied to a pellet core or tablet core, reference may be made in particular to those water-soluble layers such as are usually used before application of layers which are resistant to gastric juice, or such as are described e.g. in DE-OS 39 01 151. Examples, which may be mentioned of film polymers, which can be used for the intermediate layer are hydroxypropylmethylcellulose and/or polyvinylpyrrolidone, to which plasticizers (such as, for example, propylene glycol) and/or other additives (e.g. talc as an anti-sticking agent) and auxiliaries (e.g. buffers, bases or pigments) can also be added if desired.

In one embodiment of the invention the oral dosage form according to the invention comprises intermediate layer(s) based on hydroxypropylmethylcellulose as film polymer.

The expert knows, on the basis of his technical knowledge, what outer layers, which are resistant to gastric juice can be used. Examples of suitable polymers for the enteric coating are methacrylic acid/methyl methacrylate copolymer or methacrylic acid/ethyl-acrylate copolymer (Eudragit® L, S, or Eudragit® L30D) or cellulose derivatives, such as carboxymethylethylcellulose (CMEC, Duodcel®), cellulose acetate phthalate (CAP), cellulose acetate trimellitate (CAT), hydroxypropylmethylcellulose phthalate (HP50, HPSS), hydroxypropylmethylcellulose acetate succinate (HPMCAS) or polyvinyl acetate phthalate, to which it is also possible to add, if desired, plasticizer (such as propylene glycol or triethyl citrate) and/or other additives and ancillary substances (e.g. buffers, bases, such as, preferably, aluminum hydroxide, or pigments).

In one embodiment of the invention the oral dosage form according to the invention comprises an enteric coating based on methacrylic acid/methyl methacrylate copolymer or methacrylic acid/ethyl-acrylate copolymer. Eudragit® L30D is particularly preferred (Eudragit® L30D is composed of methacrylic acid copolymer (type C) with molecular weight 250,000, sodium dodecylsulfate and polysorbate 80).

The layers are applied in conventional ways using equipment customary for these purposes.

The oral dosage form of the invention can be manufactured for example by processes known to the skilled worker for producing tablets and pellets (for example as disclosed in the various patent documents relating to oral dosage forms for proton pump inhibitors; the process mentioned in EP-A-0 519 365 or EP-A-0 244 380 may be mentioned by way of example).

Pellets can be obtained as the case may be by application of a preliminary isolation to sucrose starter pellets and subsequent application of a 10-20% suspension of the active compound in water with polyvinylpyrrolidone (PVP) as the binder.

The isolation layer can also be applied, analogously to tablets, using corresponding ready-made dispersions (e.g. opadry) in a fluidized bed coater. The coating with a layer, which is resistant to gastric juice, is carried out by a procedure analogous to that for tablets, using fluidized bed technology.

In one embodiment of the invention, the pharmaceutical dosage form according to the invention is manufactured by producing a suspension of the magnesium salt of pantoprazole in an aqueous solution of PVP and spraying the suspension on a mixture of pharmaceutical excipients to form granules. In a preferred embodiment the PVP is low molecular weight PVP.

In the event of further processing the granules to enteric coated tablets the granules may be processed together with disintegrant and lubricant components by production processes familiar to the skilled worker to tablets and together with film former, plasticizer and coloring agent components obtaining the enteric coated tablets according to the invention.

Further subject of the invention is therefore a process for production of an oral dosage form in form of tablets or pellets containing the magnesium salt of pantoprazole comprising the following steps:
(a) production of a suspension of the magnesium salt of pantoprazole optionally together with further pharmaceutical excipients in an aqueous solution of PVP;
(b) providing a mixture of pharmaceutical excipients and
(c) granulation of the mixture obtained from (b) with the suspension obtained from (a).

In a preferred embodiment the PVP is low molecular weight PVP.

In case of dosage forms of the invention in form of tablets the granules obtained from (c) may be pressed after drying and mixing with lubricants and where applicable with further pharmaceutical excipients to tablets on a tableting machine and layered to form enteric coated tablets.

In case of dosage forms of the invention in form of multiparticulates the granules may be processed into pellets by extrusion and spheronization. Thereby the magnesium salt of pantoprazole can be suspended in the solution of PVP (a) and then mixed with other excipients (c). The mixture can be processed by extrusion/spheronization using suitable process equipments. The size of the obtained core pellets is approximately between 0.2 and 3 mm and preferably between 0.25 and 2 mm. In a preferred embodiment the PVP is low molecular weight PVP.

The manufactured extrusion pellets can further be layered with ingredients familiar to the skilled worker. The enteric coated pellets may be processed after drying by production processes familiar to the skilled worker to give enteric coated pellets which may be filled in capsules after mixing with glidants or pressed to tablets after mixing with further pharmaceutical excipients.

Alternatively, the suspension obtained from (a) may be sprayed on seeds (e.g. nonpareilles comprising sugar, cellulose or HPMC). The pellets obtained may be processed after drying by production processes familiar to the skilled worker to give enteric coated pellets which may be filled in capsules after mixing with glidants or pressed into tablets after mixing with further pharmaceutical excipients.

Particularly preferred the dosage forms of the invention in form of tablets are produced by granulating a mixture of mannitol and insoluble PVP with a suspension of the magnesium salt of pantoprazole, sodium carbonate and sodium dodecylsulfate in an aqueous solution of PVP, drying the granules, mixing with lubricant and pressing into tablets on a tableting machine, followed by the coating processes. In one embodiment the PVP is of low molecular weight.

Particularly preferred the dosage forms of the invention in form of multiparticulates based on nonpareilles-technology are produced by spraying a suspension of the magnesium salt of pantoprazole, sodium carbonate and sodium dodecylsulfate in an aqueous solution of PVP on starter pellets, drying the pellets, layering them with subcoating and enteric coating, mixing with glidants where applicable and filling into capsules. In a preferred embodiment the PVP is low molecular weight PVP.

In another embodiment which is also a particularly preferred dosage forms of the invention based on nonpareilles-technology the dosage form is produced by spraying a suspension of the magnesium salt of pantoprazole, sodium carbonate, pregelatinized starch and sodium dodecylsulfate in an aqueous solution of PVP on starter pellets, drying the pellets, layering them with subcoating and enteric coating, mixing with glidants where applicable and filling into capsules. In a preferred embodiment the PVP is low molecular weight PVP.

Particularly preferred the dosage forms of the invention in form of extrusion pellets are produced by granulating a mixture of microcrystalline cellulose, sodium carbonate, sodium starch glycolate, sodium carboxymethylcellulose with a suspension of the magnesium salt of pantoprazole in an aqueous solution of PVP, extruding the wet mass and rounding it using a spheronizer or marumerizer. The obtained pellet cores are dryed using a fluid bed dryer or other suitable drying techniques. Afterwards the pellets are layered with subcoating and gastric resistant coating, mixed with glidants where applicable and filled into capsules. In a preferred embodiment the PVP is low molecular weight PVP.

In an other embodiment of the invention the pharmaceutical form of the invention in form of tablets is produced by granulating a dry mixture of the magnesium salt of pantoprazole and pharmaceutical excipients with an aqueous solution of PVP, drying the granules and mixing them with further pharmaceutical excipients where applicable. The granules may be compressed into tablets on a tableting machine after mixing with further pharmaceutical excipients. Preferably the granulation is proceeded using a fluid bed granulator under convenient conditions. In a preferred embodiment the PVP is low molecular weight PVP.

Subject of the invention is therefore also a process to produce an oral dosage form in form of tablets or multiparticulates containing the magnesium salt of pantoprazole comprising the following steps:
(a) production of a dry mixture of the magnesium salt of pantoprazole and pharmaceutical excipients and
(b) granulating the mixture obtained from (a) with an aqueous solution of PVP.

In a preferred embodiment the PVP is low molecular weight PVP.

In case of dosage forms of the invention in form of extrusion pellets the aforementioned mixture may be processed into pellets by extrusion and spheronization. Thereby the magnesium salt of pantoprazole can be mixed with other excipients (a) and granulated with an aqueous solution of PVP (b). In a preferred embodiment the PVP is low molecular weight PVP. The mixture can be processed by extrusion/spheronization using suitable process equipments. The size of the obtained core pellets is approximately between 0.2 and 3 mm and preferably between 0.25 and 2 mm.

Particularly preferred the dosage forms of the invention in form of tablets are produced by granulating a mixture of the magnesium salt of pantoprazole, mannit and sodium carbonate and insoluble PVP using an aqueous solution of PVP, drying the granules, mixing with lubricants and pressing into tablets on a tableting machine, followed by the coating processes. In a preferred embodiment the PVP is low molecular weight PVP.

Particularly preferred the dosage forms of the invention in form of extrusion pellets are produced by granulating a dry mixture of microcrystalline cellulose, sodium carbonate, sodium starch glycolate, sodium carboxymethylcellulose and the magnesium salt of pantoprazole with an aqueous solution of PVP, extruding the wet mass and rounding it using a spheronizer or marumerizer. The obtained pellet cores are dryed using a fluid bed dryer or other suitable drying techniques, followed by the above mentioned coating processes. In a preferred embodiment the PVP is low molecular weight PVP.

The production of dosage forms according to the invention is described by way of example below. The following examples explain the invention in more detail without restricting it.

EXAMPLES

A. Synthesis of Magnesium bis[5-[difluoromethoxy]-2-[[3,4-dimethoxy-2-pyridinyl]-methyl] sulfinyl]-1H-benzimidazolide]dihydrate 3.85 kg (8.9 mol) of pantoprazole Na sesquihydrate [sodium[5-[difluoromethoxy]-2-[[3,4-dimethoxy-2-pyridinyl] methyl]sulfinyl]-1H-benzimidazolide]sesquihydrate] are dissolved at 20-25° C. in 38.5 l of purified water in a stirring vessel. A solution of 1.0 kg (4.90 mol) of magnesium dichloride hexahydrate in 8 l of purified water is added with stirring at 20-30° C. in the course of 3 to 4 h. After stirring for a further 18 h, the precipitated solid is centrifuged, washed with 23 l of purified water, stirred at 20-30° C. for 1 to 2 h in 35 l of purified water, centrifuged again and washed again with 30-50 l of purified water. The solid product is dried at 50° C. in vacuo (30-50 mbar) until a residual water content of <4.8% is achieved. The product is then ground.

The title compound is obtained as a white to beige powder, which is employed directly for further pharmaceutical processing.

Yield: 3.40 kg (90% of theory); water content: 4.5-4.6%; melting point: 194-196° C. with decomposition.

| CHN analysis | C | H | N | S |
|---|---|---|---|---|
| Theory | 46.58 | 3.91 | 10.19 | 7.77 |
| Found | 46.33 | 3.89 | 10.04 | 7.83 |

Alternatively the title compound can be produced using mixtures of organic solvents with water. For this, pantoprazole Na sesquihydrate is dissolved in an organic solvent at 50-60° C. 0.5 mole equivalents of the magnesium salt (e.g. magnesium chloride hexahydrate), dissolved in water, are added drop by drop and the solution is allowed to cool with stirring. The precipitated solid is filtered off, washed with the corresponding organic solvent and is dried in vacuo at 50° C. to constant weight. The title compound is obtained as a colourless powder. Examples for different solvents are given in the following table 1.

TABLE 1

| pantoprazole Na sesquihydrate | organic solvent | water | yield of title compound | melting point ° C. | water content % |
|---|---|---|---|---|---|
| 50 g | isopropanol 300 ml | 300 ml | 45.4 g | 196-197 | 4.4-4.5 |
| 50 g | isopropanol 300 ml | 120 ml | 45.9 g | 196-197 | 4.3 |
| 50 g | ethanol 300 ml | 300 ml | 45.8 g | 197-198 | 4.6 |
| 50 g | aceton 300 ml | 300 ml | 45.6 g | 195-196 | 4.6,-4.7 |

Alternatively the title compound can be produced by reacting pantoprazole with a basic magnesium salt, such as magnesium methylate, for example in the following manner: 90 g of pantoprazole are dissolved in 700 ml of 2-propanol at 60-70° C. 13.4 g (0.5 moles) of solid magnesium methylate are added, the solution is allowed to cool with stirring and filtered. After addition of 36 ml of water the crystalline solid formed is filtered off, washed with water and dried in vacuo at 50° C. to constant weight. The title compound of melting point 194-196° C. (water content 4.8%) is obtained as beige solid.

B. Production of Dosage Forms According to the Invention

Example B.1

Pellets Made by Wurster Coating (Nonpareilles)

I. Active Pellets

| | |
|---|---:|
| a.) Sucrose starter pellets (0.425-0.5 mm) | 500.0 g |
| b.) Sodium carbonate | 30.0 g |
| c.) Pantoprazole-Mg dihydrate | 300.0 g |
| d.) Polyvinylpyrrolidone K 25 | 35.0 g | a. is sprayed with an aqueous dispersion of b., c. and d. in a fluidised bed process (Wurster equipment) or other suitable equipments (e.g. coating pan).

II. Intermediate Layer (Subcoating)

| | |
|---|---:|
| e.) Hydroxypropylmethylcellulose | 120.0 g |
| f.) Titanium dioxide | 2.0 g |
| g.) LB Iron oxide yellow | 0.2 g |
| h.) Propylene glycol | 24.0 g | e. is dissolved in water (A). f. and g. are suspended in water using a high shear mixer (B). A and B are combined and after addition of h. the resulting suspension is sieved through a suitable sieve. The suspension is sprayed onto 500 g of the active pellets obtained under I using a fluidised bed process (Wurster) or other suitable processes (e.g. coating pan).

III. Coating with a Layer which is Resistant to Gastric Juice (Enteric Coating)

| | |
|---|---:|
| i.) Eudragit ® L 30 D | 230.0 g |
| j.) Triethyl citrate | 7.0 g | i. is suspended in water and after addition of j. the resulting dispersion is sieved through a suitable sieve. III is sprayed onto 500 g of the isolated pellets obtained under II in a Wurster fluidised bed-apparatus or other suitable equipments (e.g. coating pan).

The resulting enteric coated pellets could be filled in hard gelatine capsules of suitable size (e.g. size 2) or tableted using suitable tableting ingredients (e.g. microcrystalline cellulose or lactose monohydrate) on a prevalent tablet press (see examples B6/7).

Example B.2

Pellets Made by Wurster Coating (Nonpareilles)

I. Active Pellets

| | |
|---|---:|
| a.) Cellulose pellets (0.6-0.7 mm) | 1000.0 g |
| b.) Sodium carbonate | 75.0 g |
| c.) Pantoprazole-Mg dihydrate | 650.0 g |
| d.) Polyvinylpyrrolidone K 25 | 80.0 g | a. is sprayed with an aqueous dispersion of b., c. and d. in a fluidised bed process (Wurster equipment) or other suitable equipments (e.g. coating pan).

II. Intermediate Layer (Subcoating)

| | |
|---|---:|
| e.) Hydroxypropylmethylcellulose | 250.0 g |
| f.) Titanium dioxide | 5.0 g |
| g.) LB Iron oxide yellow | 0.45 g | e. is dissolved in water (A). f. and g. are suspended in water using a high shear mixer (B). A and B are combined and the resulting suspension is sieved through a suitable sieve. The suspension is sprayed onto 1000 g of the active pellets obtained under I using a fluidised bed process (Wurster) or other suitable processes (e.g. coating pan).

III. Coating with a Layer which is Resistant to Gastric Juice (Enteric Coating)

| | |
|---|---:|
| h.) Eudragit ® L 30 D | 365.0 g |
| i.) Triethyl citrate | 15.0 g | h. is suspended in water and after addition of i. the resulting dispersion is sieved through a suitable sieve. III is sprayed onto 1000 g of the isolated pellets obtained under II in a Wurster fluidised bed-apparatus or other suitable equipments (e.g. coating pan).

The resulting enteric coated pellets could be filled in hard gelatine capsules of suitable size (e.g. size 2) or tableted using suitable tableting ingredients (e.g. microcrystalline cellulose or lactose monohydrate) on a prevalent tablet press (see examples B6/7).

Example B.3

Pellets Made by Wurster Coating (Nonpareilles)

I. Active Pellets

| | |
|---|---:|
| a.) Cellulose pellets (0.4-0.5 mm) | 2000.0 g |
| b.) Sodium carbonate | 136.0 g |
| c.) Pantoprazole-Mg dihydrate | 1420.0 g |
| d.) Polyvinylpyrrolidone K 25 | 117.0 g |
| e.) Sodium dodecylsulfate (SDS) | 16.4 g |

To produce core material, suspension layering is performed in a fluid bed apparatus or other suitable equipment as described in example B1.

II. Intermediate Layer (Subcoating)

| | |
|---|---:|
| f.) Hydroxypropylmethylcellulose | 600.0 g |
| g.) Polyvinylpyrrolidone K 25 | 8.0 g |
| h.) Titanium dioxide | 10.0 g |
| i.) LB Iron oxide yellow | 1.0 g |

The pellets covered with intermediate layer are produced as described in example B1.

III. Coating with a Layer which is Resistant to Gastric Juice (Enteric Coating)

| | |
|---|---:|
| j.) Hydroxypropylmethylcellulose acetate succinate | 800.0 g |
| k.) Triethyl citrate | 250.0 g |
| l.) Ethanol | 7250.0 g |

The enteric coating layer is applied to the isolated pellets using fluidized bed equipment from a water/ethanol solution.

The resulting enteric coated pellets could be filled in hard gelatine capsules of suitable size (e.g. size 2) or tableted using suitable tableting ingredients (e.g. microcrystalline cellulose or lactose monohydrate) on a prevalent tablet press (see examples B6/7).

Example B.4

Pellets Made by Extrusion/Spheronization

I. Manufacture of Pellets Using Extrusion/Spheronization

| | |
|---|---:|
| a.) Pantoprazole-Mg dihydrate | 250.0 g |
| b.) Microcrystalline cellulose | 150.0 g |
| c.) Sodium starch glycolate | 20.0 g |
| d.) Sodium carbonate | 32.5 g |
| e.) Sodium carboxymethylcellulose | 25.0 g |
| f.) Polyvinylpyrrolidone K 25 | 35.0 g | a.-c. are mixed using a suitable mixer. d.-f. are dissolved in water and the resulting binder solution is added to the powder mixture. After addition of the solution and mixing the mass is extruded using a screw extruder. Afterwards the granules are rounded using a spheronizer and dryed in a fluidised bed apparatus.

II. Intermediate Layer (Subcoating)

The application of the intermediate layer is carried out by a procedure analogus to that described for the nonpareilles pellets (example B1 to B3) using fluidised bed or other suitable equipment.

III. Coating with a Layer which is Resistant to Gastric Juice

The application of the gastric resistant layer is carried out by a procedure analogus to that described for the nonpareilles pellets (example B1 to B3) using fluidised bed or other suitable equipment.

The resulting enteric coated pellets could be filled in hard gelatine capsules of suitable size (e.g. size 2) or tableted using suitable tableting ingredients (e.g. microcrystalline cellulose or lactose monohydrate) on a prevalent tablet press (see examples B6/7).

Example B.5

Pellets Made by Extrusion/Spheronization

I. Manufacture of Pellets Using Extrusion/Spheronization

| | |
|---|---:|
| a.) Pantoprazole-Mg dihydrate | 1300.0 g |
| b.) Microcrystalline cellulose | 700.0 g |
| c.) Lactose monohydrate | 150.0 g |
| d.) Hydroxypropylmethylcellulose | 110.0 g |
| e.) Sodium carbonate | 180.0 g |
| f.) Pregelatinized starch | 125.0 g |
| g.) Polyvinylpyrrolidone K 25 | 200.0 g |

The extrusion pellets are produced as described in example B4.

II. Intermediate Layer (Subcoating)

The application of the intermediate layer is carried out by a procedure analogus to that described for the nonpareilles pellets (example B1 to B3) using fluidised bed or other suitable equipment.

III. Coating with a Layer which is Resistant to Gastric Juice

The application of the gastric resistant layer is carried out by a procedure analogus to that described for the nonpareilles pellets (example B1 to B3) using fluidised bed or other suitable equipment.

The resulting enteric coated pellets could be filled in hard gelatine capsules of suitable size (e.g. size 2) or tableted using suitable tableting ingredients (e.g. microcrystalline cellulose or lactose monohydrate) on a prevalent tablet press (see examples B6/7).

Example B.6

Multiple Unit Tableted Dosage Form Made from Nonpareilles-Pellets

I. Active Pellets

| | |
|---|---:|
| a.) Cellulose pellets (0.6-0.7 mm) | 2500.0 g |
| b.) Sodium carbonate | 180.0 g |
| c.) Pantoprazole-Mg dihydrate | 1700.0 g |
| d.) Polyvinylpyrrolidone K 25 | 250.0 g |
| e.) Sodium dodecylsulfate | 18.0 g | a. is sprayed with an aqueous dispersion of b., c., d. and e. in a fluidized bed process (Wurster equipment) or other suitable equipments (e.g. coating pan).

II. Intermediate Layer (Subcoating)

| | |
|---|---|
| f.) Hydroxypropylmethylcellulose | 600.0 g |
| g.) Talcum (micronized) | 100.0 g |
| h.) Magnesium stearate | 80.0 g | f. is dissolved in water (A). g. and h. are suspended in water using a high shear mixer (B). A and B are combined and the resulting suspension is sieved through a suitable sieve. The suspension is sprayed onto 2500 g of the active pellets obtained under I using a fluidised bed process (Wurster) or other suitable processes (e.g. coating pan).

III. Coating with a Layer which is Resistant to Gastric Juice (Enteric Coating)

| | |
|---|---|
| i.) Methacrylic acid copolymer | 925.0 g |
| j.) Polyethylene glycole 400 | 28.0 g | i. is suspended in water and after addition of j. the resulting dispersion is sieved through a suitable sieve. III is sprayed onto 2500 g of the isolated pellets obtained under II in a Wurster fluidised bed-apparatus or other suitable equipments (e.g. coating pan).

IV. Tablets

| | |
|---|---|
| k.) Microcrystalline cellulose | 3750.0 g |
| l.) Crosslinked polyvinylpyrrolidone | 100.0 g |
| m.) Magnesium stearate | 7.0 g |

2500 g of enteric coated pellets are mixed with the tableting excipients and compressed into tablets using a single punch tableting machine equipped with 11 mm round punches. The amount of pantoprazole is approx. 20 mg.

Example B.7

Multiple Unit Tableted Dosage Form Made from Extrusion-Pellets

I. Manufacture of Pellets Using Extrusion/Spheronization

| | |
|---|---|
| a.) Pantoprazole-Mg dihydrate | 433.0 g |
| b.) Microcrystalline cellulose | 240.0 g |
| c.) Lactose monohydrate | 55.0 g |
| d.) Hydroxypropylmethylcellulose | 35.0 g |
| e.) Sodium carbonate | 60.0 g |
| f.) Sodium dodecylsulfate | 5.5 g |
| g.) Pregelatinized starch | 35.0 g |
| h.) Polyvinylpyrrolidone K 25 | 70.0 g |

The extrusion pellets are produced as described in example B5.

II. Intermediate Layer (Subcoating)

| | |
|---|---|
| i.) Hydroxypropylmethylcellulose | 190.0 g |
| j.) Polyvinylpyrrolidone K 25 | 8.0 g |

-continued

| | |
|---|---|
| j.) Talcum (micronized) | 32.0 g |
| k.) Magnesium stearate | 14.0 g |

The application of the intermediate layer is carried out by a procedure analogus to that described for the nonpareilles pellets (example B1 to B3) using fluidised bed or other suitable equipment.

III. Coating with a Layer which is Resistant to Gastric Juice (Enteric Coating)

| | |
|---|---|
| l.) Methacrylic acid copolymer | 296.0 g |
| m.) Glycerol triacetate | 28.0 g |

The application of the gastric resistant layer is carried out by a procedure analogus to that described for the nonpareilles pellets (example B1 to B3) using fluidised bed or other suitable equipment.

IV. Tablets

| | |
|---|---|
| n.) Microcrystalline cellulose | 1200.0 g |
| o.) Crosslinked polyvinylpyrrolidone | 32.0 g |
| p.) Polyethyleneglycole 4000 | 38.0 g |
| q.) Magnesium stearate | 4.5 g |

The enteric coated extrusion pellets are tableted with the above tableting excipients as described in example B6 of an amount of approximately 40 mg pantoprazole.

Example B.8

Tablets

I. Tablet Core

| | |
|---|---|
| a.) Pantoprazole-Mg dihydrate | 43.04 mg |
| b.) Sodium carbonate | 5.55 mg |
| c.) Mannitol | 52.66 mg |
| d.) Crospovidone | 40.00 mg |
| e.) Polyvinylpyrrolidone K 25 | 5.00 mg |
| f.) Purified water | 7.42 mg |
| g.) Calcium stearate | 3.00 mg | a. is dry-mixed with a part of b., a part of c. and d. and put in the vessel of a fluid bed granulator; e. is dissolved in f. together with the other part of b. and c. to form the granulation liquid. The solution is sprayed on the mixture under convenient conditions. After drying and mixing with g. the mixture is pressed into tablets using a rotary tableting machine equipped with 7 mm round punches. Tablet weight is approx. 156.7 mg, corresponding to 40 mg pantoprazole (i.e. 43.04 mg pantoprazole-Mg dihydrate).

II. Intermediate Layer (Subcoating)

| | |
|---|---|
| h.) Hydroxypropylmethylcellulose | 11.87 mg |
| i.) Polyvinylpyrrolidone K 25 | 0.24 mg |
| j.) Titanium dioxide | 0.21 mg |

| | |
|---|---|
| k.) LB Iron oxide yellow | 0.02 mg |
| l.) Propylene glycol | 2.66 mg | h. is dissolved in water (A). j. and k. are suspended in a solution of i. in water using a high shear mixer (B). After sieving of B, A and B are combined l. is added to the suspension. The suspension is sprayed onto the tablet cores obtained under I using a coating pan.

III. Coating with a Layer which is Resistant to Gastric Juice (Enteric Coating)

| | |
|---|---|
| m.) Eudragit ® L 30 D | 7.27 mg |
| n.) Triethyl citrate | 0.73 mg | n. is suspended in water and mixed m. III is sprayed onto the isolated tablets obtained under II using a coating pan.

Example B.9

Tablets

I. Tablet Core

| | |
|---|---|
| a.) Pantoprazole-Mg dihydrate | 43.04 mg |
| b.) Sodium carbonate | 5.55 mg |
| c.) Mannitol | 51.94 mg |
| d.) Crospovidone | 40.00 mg |
| e.) Polyvinylpyrrolidone K 25 | 5.00 mg |
| f.) Sodium dodecylsulfate | 0.72 mg |
| g.) Purified water | 7.42 mg |
| h.) Calcium stearate | 3.00 mg | f. and a part of b. are dissolved in water, a part of c. is added and a. is suspended in the solution. A solution of e. in water is added to the suspension. The other part of b. and c. is mixed with d. and the mixture is put in the vessel of a fluid bed granulator. The suspension is sprayed on the mixture under convenient conditions. After drying and mixing with h. the mixture is compressed into tablets using a rotary tableting machine equipped with 7 mm round punches. Tablet weight is approx. 156.7 mg.

The tablet cores are isolated and layered with an enteric coating as described in Example B8.

Example B.10

Tablets

I. Tablet Core

| | |
|---|---|
| a.) Pantoprazole-Mg dihydrate | 43.04 mg |
| b.) Sodium carbonate | 5.55 mg |
| c.) Mannitol | 52.66 mg |
| d.) Crospovidone | 40.00 mg |
| e.) Polyvinylpyrrolidone K 30 | 5.00 mg |
| f.) Purified water | 7.42 mg |
| g.) Calcium stearate | 3.00 mg |

The tablet cores are produced as described in example B8. The tablet cores are layered with an isolating coating and an enteric coating as described in example B8.

Example B.11

Tablets

I. Tablet Core

| | |
|---|---|
| a.) Pantoprazole-Mg dihydrate | 43.04 mg |
| b.) Sodium carbonate | 5.55 mg |
| c.) Mannitol | 52.66 mg |
| d.) Crospovidone | 40.00 mg |
| e.) Polyvinylpyrrolidone K 17 | 5.00 mg |
| f.) Purified water | 7.42 mg |
| g.) Calcium stearate | 3.00 mg |

The tablet cores are produced as described in example B8. The tablet cores are layered with an isolating coating and an enteric coating as described in example B8.

Example B.12

Tablets

I. Tablet Core

| | |
|---|---|
| a.) Pantoprazole-Mg dihydrate | 43.04 mg |
| b.) Sodium carbonate | 5.55 mg |
| c.) Mannitol | 52.66 mg |
| d.) Crospovidone | 40.00 mg |
| e.) Polyvinylpyrrolidone K 12 | 5.00 mg |
| f.) Purified water | 7.42 mg |
| g.) Calcium stearate | 3.00 mg |

The tablet cores are produced as described in example B8. The tablet cores are layered with an isolating coating and an enteric coating as described in example B8.

Example B.13

Tablets

I. Tablet Core

| | |
|---|---|
| a.) Pantoprazole-Mg dihydrate | 43.04 mg |
| b.) Sodium carbonate | 5.55 mg |
| c.) Lactose | 55.00 mg |
| d.) Crospovidone | 35.00 mg |
| e.) Polyvinylpyrrolidone K 25 | 5.00 mg |
| f.) Purified water | 7.42 mg |
| g.) Calcium stearate | 3.00 mg |

The tablet cores are produced as described in example B8. Tablet weight approx. 154 mg.

II. Intermediate Layer (Subcoating)

| | |
|---|---|
| h.) Hydroxypropylmethylcellulose | 12.20 mg |
| i.) Titanium dioxide | 0.21 mg |
| j.) LB Iron oxide yellow | 0.02 mg | h. is dissolved in water (A). i. and j. are suspended in water using a high shear mixer (B). A and B are combined and the resulting suspension is sieved through a suitable sieve. The suspension is sprayed onto the tablet cores obtained under I using a coating pan.

The isolated tablet cores are layered with an enteric coating as described in example B8.

Example B.14

Tablets

I. Tablet Core

| | |
|---|---|
| a.) Pantoprazole-Mg dihydrate | 43.04 mg |
| b.) Trinatriumphosphate | 5.55 mg |
| c.) Mannitol | 55.00 mg |
| d.) Crospovidone | 40.00 mg |
| e.) Polyvinylpyrrolidone K 25 | 5.00 mg |
| f.) Purified water | 7.42 mg |
| g.) Magnesium stearate | 3.00 mg |

The tablet cores are produced as described in example B8. Tablet weight approx. 159 mg.

II. Intermediate Layer (Subcoating)

The tablet cores are layered with an isolating coating as described in example B8.

III. Coating with a Layer which is Resistant to Gastric Juice (Enteric Coating)

| | |
|---|---|
| m.) Methacrylic acid copolymer | 6.5 mg |
| n.) Glycerol triacetate | 0.65 mg |

The application of the gastric resistant layer is carried out as described in example B8.

Example B.15

I. Tablet Core

| | |
|---|---|
| a) Pantoprazole-Mg dihydrate | 43.04 mg |
| b) Sodium carbonate | 5.55 mg |
| c) Mannitol | 52.66 mg |
| d) Crospovidone | 40.00 mg |
| e) PVP 90 (povidone) | 5.00 mg |
| f) Calcium stearate | 3.00 mg | a) is mixed with some of b), c) and the complete amount of d). The remainders of b) and c) are added to a clear aqueous solution of e). Granules are obtained with this solution in a fluidized bed. f) is added to the dry granules and the granules are pressed on a suitable tablet-press.

II. Preliminary Isolation (Intermediate Layer)

| | |
|---|---|
| g) HPMC 2910, 3 cps | 11.87 mg |
| h) PVP 25 | 0.24 mg |
| i) Titanium dioxide | 0.21 mg |
| j) Iron oxide yellow 100 E 172 | 0.02 mg |
| k) Propylene glycol | 2.66 mg |
| Total weight per preisolated core | 172 mg | g) is dissolved in water and h) is added and also dissolved (A). i) and j) are suspended in water using a suitable stirrer (B). A and B are combined. After addition of k), the suspension is sieved immediately before further processing, during which the tablet cores obtained under I. are coated to an adequate thickness of the intermediate layer in a suitable coating apparatus.

III. Coating with a Layer which is Resistant to Gastric Juice

| | |
|---|---|
| l) Eudragit L 30 D | 7.27 mg |
| m) Triethyl citrate | 0.73 mg |
| Total weight per film-coated tablet resistant to gastric juice | 180 mg | l) is diluted with water and m) is added. The dispersion is sieved before processing.

The preisolated tablets are sprayed in suitable coating apparatuses using the obtained dispersion.

Example B.16

Pellets Made by Wurster Coating (Nonpareilles)

I. Active Pellets

| | |
|---|---|
| a.) Sucrose starter pellets (0.71-0.85 mm) | 4.0 kg |
| b.) Sodium carbonate | 0.27 kg |
| c.) Pantoprazole-Mg dihydrate | 2.84 kg |
| d.) Polyvinylpyrrolidone K 25 | 0.23 kg |
| e.) Pregelatinized starch | 0.22 kg |
| f.) Sodium dodecylsulfate | 0.03 kg | a. is sprayed with an aqueous dispersion of the other ingredients in a fluidised bed process (Wurster equipment) or other suitable equipments (e.g. coating pan).

II. Intermediate Layer (Subcoating)

| | |
|---|---|
| g.) Hydroxypropylmethylcellulose | 1.830 kg |
| h.) Titanium dioxide | 0.028 kg |
| i.) LB Iron oxide yellow | 0.003 kg |
| j.) Polyvinylpyrrolidone K25 | 0.021 kg | g. and j. are dissolved in water (A). h. and i. are suspended in water using a high shear mixer (B). A and B are combined and the resulting suspension is sieved through a suitable sieve. The suspension is sprayed onto the active pellets obtained under I using a fluidised bed process (Wurster) or other suitable processes (e.g. coating pan).

III. Coating with a Layer which is Resistant to Gastric Juice (Enteric Coating)

| | |
|---|---|
| k.) Eudragit ® L 30 D | 4.40 kg |
| l.) Triethyl citrate | 0.13 kg |
| m.) Talcum | 0.06 kg | k. is suspended in water and after addition of l. the resulting dispersion is sieved through a suitable sieve. The dispersion is sprayed on the isolated pellets obtained under II in a Wurster fluidised bed-apparatus or other suitable equipments (e.g. coating pan).

The resulting enteric coated pellets are mixed with talcum (m) and could be filled in hard gelatine capsules of suitable size (e.g. size 2) or tabletted using suitable tableting ingredients (e.g. microcrystalline cellulose or lactose monohydrate) on a prevalent tablet press.

C. Physical Investigations and Comparative Tests with Dosage Forms in which High Molecular Weight PVP was Used as Binder

Example C.1

Tablets

I. Tablet Core

| | |
|---|---|
| a.) Pantoprazole-Mg dihydrate | 43.04 mg |
| b.) Sodium carbonate | 5.55 mg |
| c.) Mannitol | 52.66 mg |
| d.) Crospovidone | 40.00 mg |
| e.) Polyvinylpyrrolidone K 90 | 5.00 mg |
| f.) Purified water | 7.42 mg |
| g.) Magnesium stearate | 3.00 mg |

The tablet cores are produced as described in example B8. The tablet cores are layered with an Isolating coating and an enteric coating as described in example B8.

Example C.2

I. Tablet Core

| | |
|---|---|
| a) Pantoprazole-Na sesquihydrate | 45.10 mg |
| b) Sodium carbonate | 10.00 mg |
| c) Mannitol | 42.70 mg |
| d) Crospovidone | 50.00 mg |
| e) PVP 90 (povidone) | 4.00 mg |
| f) Calcium stearate | 3.20 mg | a) is mixed with some of b), c) and d). The remainders of b) and c) are added to a clear aqueous solution of e). Granules are obtained with this solution in a fluidized bed. The remainder of d) and f) are added to the dry granules and the granules are pressed on a suitable tablet press.

II. Preliminary Isolation (Intermediate Layer)

| | |
|---|---|
| g) HPMC 2910, 3 cps | 19.00 mg |
| h) PVP 25 | 0.38 mg |
| i) Titanium dioxide | 0.34 mg |
| j) Iron oxide yellow 100 E 172 | 0.03 mg |
| k) Propylene glycol | 4.25 mg |
| Total weight per preisolated core | 188 mg | g) is dissolved in water and h) is added and also dissolved (A). i) and j) are suspended in water using a suitable stirrer (B). A and B are combined. After addition of k), the suspension is sieved immediately before further processing, during which the tablet cores obtained under I. are coated to an adequate thickness of the intermediate layer in a suitable coating apparatus.

III. Coating with a Layer which is Resistant to Gastric Juice

| | |
|---|---|
| l) Eudragit L 30 D | 14.56 mg |
| m) Triethyl citrate | 1.45 mg |
| Total weight per film-coated tablet resistant to gastric juice | 204 mg | l) is diluted with water and m) is added. The dispersion is sieved before processing.

The preisolated tablets are sprayed in suitable coating apparatuses using the obtained dispersion.

The release of the magnesium salt of pantoprazole was determined for tablet cores corresponding to example B8, B9, B10, B11 and B12 compared to a tablet core corresponding to example C1.

Disintegration of tablet cores: the disintegration of tablet cores was determined as described in the European Pharmacopoeia.

Release of active ingredient: the release of active ingredient was determined as described in the US Pharmacopoeia (USP XXV; apparatus 2; phosphate buffer pH 6.8; 100 rpm).

Figure 2:
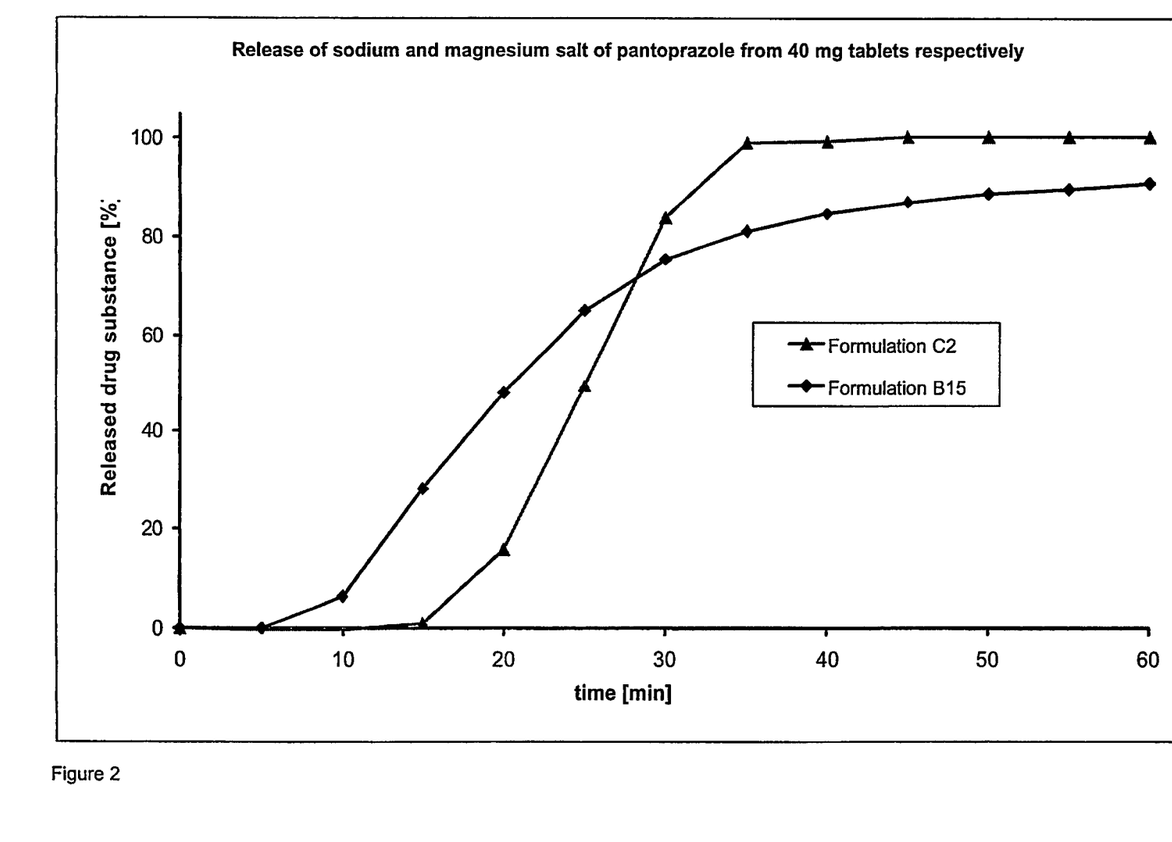
FIG. 2 shows the difference in release of the magnesium salt of pantoprazole from a tablet compared to the release of the sodium salt of pantoprazole from a tablet with comparable composition.

The release of the formulations according to example B15 and C2 was determined after 2 hours in 0.1 N hydrochloric acid and 1 hour in phosphate buffer pH 6.8; 100 rpm). In FIG. 2 only the drug release in phosphate buffer is shown.

Figure 1:
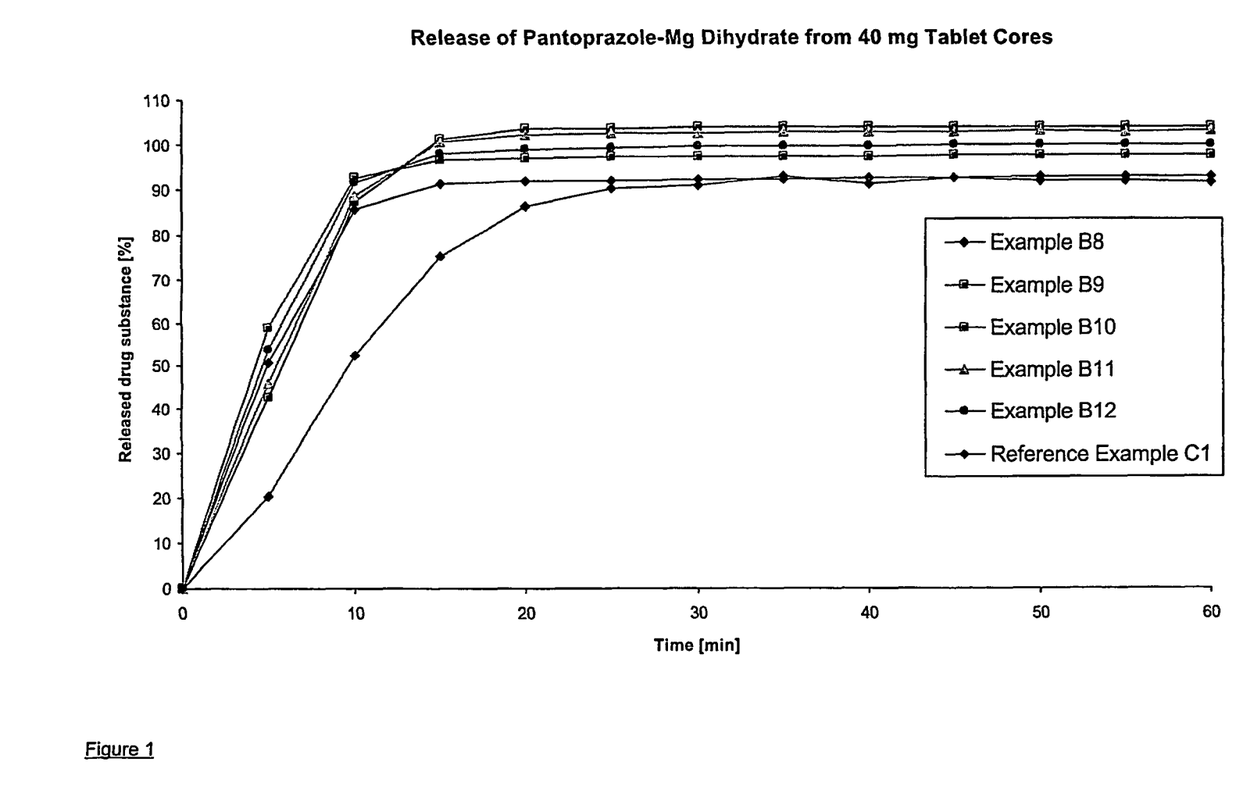
FIG. 1 shows the release of the magnesium salt of pantoprazole from tablet cores containing different types of PVP with different molecular weights. The granules of example B9 were produced by granulating them using a suspension of the magnesium salt of pantoprazole in an aqueous solution of PVP. The granules of the examples B8, B10, B1, B12 and the reference example C1 were produced by granulating a dry mixture of the magnesium salt of pantoprazole and pharmaceutical excipients using an aqueous solution of PVP.

Result: The disintegration results are shown in Table 1, the dissolution profiles are shown in FIG. 1.

TABLE 1

| Example | PVP used as binder | Disintegration [min] |
|---|---|---|
| B8 | PVP 25 | 7 |
| B9 | PVP 25 | 6.5 |
| B10 | PVP 30 | 10.5 |
| B11 | PVP 17 | 9 |
| B12 | PVP 12 | 7.5 |
| C1 | PVP 90 | 10.5 |

Surprisingly, the dissolution of the magnesium salt of pantoprazole from tablet cores in which low molecular weight PVP was used as binder is faster than from tablet cores in which high molecular weight PVP was used although the disintegration for all tablet cores is below 15 minutes.

D. Physical Investigations and Comparative Tests with Dosage Forms Containing Pantoprazole Sodium Sesquihydrate and Pantoprazole Magnesium Dihydrate FIG. 2 shows the difference in release of the magnesium salt of pantoprazole from a tablet compared to the release of the sodium salt of pantoprazole from a tablet with comparable composition. The dosage form having the sodium salt of pantoprazole as active ingredient (example C.2) shows after a short lag time an immediate and complete release of the active ingredient. Surprisingly the dosage form containing the magnesium salt of pantoprazole does not have a lag time in release of active compound and shows a constant release of active ingredient over whole period.

E. Results of Clinical Study

Healing of patient suffering from GERD (gastro-oesophageal reflux disease) I to III (according to Savary/Miller classification modified by Siewert) after treatment with pantoprazole magnesium dihydrate 40 mg o.d. (dosage form according to the invention) in comparison with a corresponding pantoprazole sodium sesquihydrate 40 mg o.d. dosage form have been studied. Surprisingly it has been found that pantoprazole magnesium dihydrate formulation is superior to pantoprazole sodium sesquihydrate formulation in the healing of GERD I to III, whereby safety is comparable for both dosage forms.

INDUSTRIAL APPLICABILITY

The dosage forms according to the invention containing the magnesium salt of pantoprazole can be employed for the treatment and prevention of all the diseases, which are regarded as treatable or avoidable by the use of pyridin-2-ylmethylsulfinyl-1H-benzimidazoles. In particular, such dosage forms according to the invention can be employed in the treatment of stomach disorders. Examples which may be mentioned in connection with the invention are the treatment or prophylaxis of benign gastric ulcer, gastro-oesophageal reflux disease, Zollinger-Ellison syndrome, duodenal ulcer, duodenal ulcer associated with *Helicobacter pylori*, prophylaxis of NSAID-associated gastric or duodenal ulcer in patients with an increased risk of gastroduodenal complication who require continued NSAID treatment or combination therapy with antibiotics in the eradication of *Helicobacter pylori*. Such dosage forms according to the invention contain between 1 and 500 mg, preferably between 5 and 100 mg, particularly preferable between 5 and 80 mg of the pantoprazole. Examples which may be mentioned are tablets or capsules which contains the pantoprazole magnesium salt in an amount corresponding to 10, 20, 40, 50, 80 or 100 mg of pantoprazole (free acid). The administration of the daily dose (e.g. 40 mg of active compound) can be carried out, for example, in the form of an individual dose or by means of a number of doses of the administration forms according to the invention (e.g. 2 times 20 mg of active compound).

The invention therefore also relates to a method for the prophylaxis or treatment of a clinical condition in a mammal, such as a human, for which a proton pump inhibitor is indicated, which comprises administration of a therapeutically effective amount pantoprazole magnesium in a dosage form according to the invention. In one embodiment the clinical condition is selected from the group of benign gastric ulcer, gastro-oesophageal reflux disease, Zollinger-Ellison syndrome, duodenal ulcer, duodenal ulcer associated with *Helicobacter pylori*, prophylaxis of NSAID-associated gastric or duodenal ulcer in patients with an increased risk of gastroduodenal complication who require continued NSAID treatment and combination therapy with antibiotics in the eradication of *Helicobacter pylori*. In a preferred embodiment the clinical condition is gastro-oesophageal reflux disease (GERD), in particular GERD I to III (according to Savary/Miller classification, optionally modified according to Siewert).

The dosage forms according to the invention can be combined with other medicaments, either in various combinations or in a fixed combination. In connection with the administration forms according to the invention, which contain magnesium salt of pantoprazole as active compounds, combinations with antimicrobial active compounds and combinations with NSAIDs (nonsteroidal antiinflammatory drugs) are particularly worthy of mention. Combination with antimicrobial agents, such as are employed for the control of the microorganism *Helicobacter pylori* (*H. pylori*), may particularly be mentioned.

Examples of suitable antimicrobial active compounds (active against *Helicobacter pylori*) are described in EP-A-0 282 131. Examples of antimicrobial agents suitable for the control of the microorganism *Helicobacter pylori* which may be mentioned are, for example, bismuth salts [e.g. bismuth subcitrate, bismuth subsalicylate, ammonium bismuth(III) potassium citrate dihydroxide, bismuth nitrate oxide, dibismuth tris(tetraoxodialuminate)], but in particular β-lactam antibiotics, for example penicillins (such as benzylpenicillin, phenoxymethylpenicillin, propicillin, azidocillin, dicloxacillin, flucloxacillin, oxacillin, amoxicillin, bacampicillin, ampicillin, mezlocillin, piperacillin or azlocillin), cephalosporins (such as cefadroxil, cefaclor, cefalexin, cefixime, cefuroxime, cefetamet, cefadroxil, ceftibuten, cefpodoxime, cefotetan, cefazolin, cefoperazon, ceftizoxime, cefotaxime, ceftazidime, cefamandol, cefepime, cefoxitin, cefodizime, cefsulodin, ceftriaxon, cefotiam or cefmenoxime) or other β-lactam antibiotics (e.g. aztreonam, loracarbef or meropenem); enzyme inhibitors, for example sulbactam; tetracyclines, for example tetracycline, oxytetracycline, minocycline or doxycycline; aminoglycosides, for example tobramycin, gentamicin, neomycin, streptomycin, amikacin, netilmicin, paromomycin or spectinomycin; amphenicols, for example chloramphenicol or thiamphenicol; lincomycins and macrolide antibiotics, for example clindamycin, lincomycin, erythromycin, clarithromycin, spiramycin, roxithromycin or azithromycin; polypeptide antibiotics, for example colistin, polymixin B, teicoplanin or vancomycin; gyrase inhibitors, for example norfloxacin, cinoxacin, ciprofloxacin, pipemidic acid, enoxacin, nalidixic acid, pefloxacin, fleroxacin or ofloxacin; nitroimidazoles, for example metronidazole; or other antibiotics, for example fosfomycin or fusidic acid. Particularly worthy of mention in this connection is the administration of the magnesium salt of pantoprazole with the combination of a multiplicity of antimicrobial active compounds, for example with the combination of a bismuth salt and/or tetracyclines with metronidazole or the combination of amoxicillin or clarithromycin with metronidazole and amoxicillin with clarithromycin.

The invention claimed is:

1. A dosage form for oral administration in tablet form consisting of:
    (a) a core consisting of:
        i. pantoprazole magnesium dihydrate,
        ii. 5.55 mg of sodium carbonate,
        iii. 52.66 mg of mannitol,
        iv. 40.00 mg of crospovidone,
        v. 5.00 mg of PVP 90, and
        vi. 3.00 mg of calcium stearate;
    (b) an intermediate layer surrounding the core, the intermediate layer formed from a mixture consisting of hydroxypropylmethylcellulose, PVP 25, titanium dioxide, iron oxide yellow and propylene glycol; and
    (c) an outer layer surrounding the intermediate layer, the outer layer formed from a mixture consisting of methacrylic acid copolymer, sodium dodecylsulfate, polysorbate 80 and triethyl citrate.

2. The dosage form according to claim 1 containing between 5 and 100 mg of pantoprazole magnesium dihydrate.

3. The dosage form according to claim 2, which contains an amount of pantoprazole magnesium dihydrate which corresponds to 10, 20, 40, 50, 80 or 100 mg of pantoprazole.

4. The dosage form according to claim 3, which contains an amount of pantoprazole magnesium dihydrate which corresponds to 80 mg of pantoprazole.

5. A method for the prophylaxis or treatment of a clinical condition in a mammal for which a proton pump inhibitor is indicated, which comprises administration of a therapeutically effective amount of pantoprazole magnesium dihydrate in a dosage form according to claim 1.

6. The method of treatment according to claim 5, wherein the clinical condition is selected from the group consisting of benign gastric ulcer, gastro-oesophageal reflux disease, Zollinger-Ellison syndrome, duodenal ulcer, duodenal ulcer associated with *Helicobacter pylori*, and prophylaxis of NSAID-associated gastric or duodenal ulcer in patients with an increased risk of gastroduodenal complication who require continued NSAID treatment and combination therapy with antibiotics in the eradication of *Helicobacter pylori*.

7. The dosage form according to claim 3, which contains an amount of pantoprazole magnesium dihydrate which corresponds to 40 mg of pantoprazole.

8. The method of treatment according to claim 6, wherein the clinical condition is gastrooesophageal reflux disease (GERD).

9. The method of treatment according to claim 8, wherein the clinical condition is selected from the group consisting of GERD I, GERD III and GERD III (according to Savary/Miller Classification).

* * * * *